United States Patent [19]

Rising et al.

[11] Patent Number: 4,525,182
[45] Date of Patent: Jun. 25, 1985

[54] I.V. FILTER APPARATUS

[75] Inventors: Donald B. Rising, Stow; Richard G. Naegeli, Jr., Bedford, both of Mass.

[73] Assignee: Millipore Corporation, Bedford, Mass.

[21] Appl. No.: 527,546

[22] Filed: Aug. 29, 1983

[51] Int. Cl.³ ............................................. B01D 19/00
[52] U.S. Cl. ...................................... 55/159; 210/436
[58] Field of Search ................. 55/159, 318; 210/188, 210/436

[56]  References Cited
U.S. PATENT DOCUMENTS 3,523,408  8/1970  Rosenberg ............................. 55/159
4,336,036  6/1982  Leeke et al. ........................... 55/159

FOREIGN PATENT DOCUMENTS 1221625  2/1971  United Kingdom ................. 55/159

Primary Examiner—Charles Hart
Attorney, Agent, or Firm—Andrew T. Karnakis; Paul J. Cook

[57] ABSTRACT

A filter apparatus is provided which is adapted for filtration of intravenous liquids and separates gas in the incoming intravenous liquid prior to delivering the filtered liquid to a patient. Incoming liquid is passed into a space within a filter holder, which space has a smaller portion that excludes gas due to surface tension forces and a larger portion where gas accumulates. A hydrophobic filter membrane is positioned adjacent the large portion of the space to permit passage of gas from the space. A hydrophilic filter membrane is positioned within the space to filter the liquid prior to administration to the patient.

10 Claims, 6 Drawing Figures

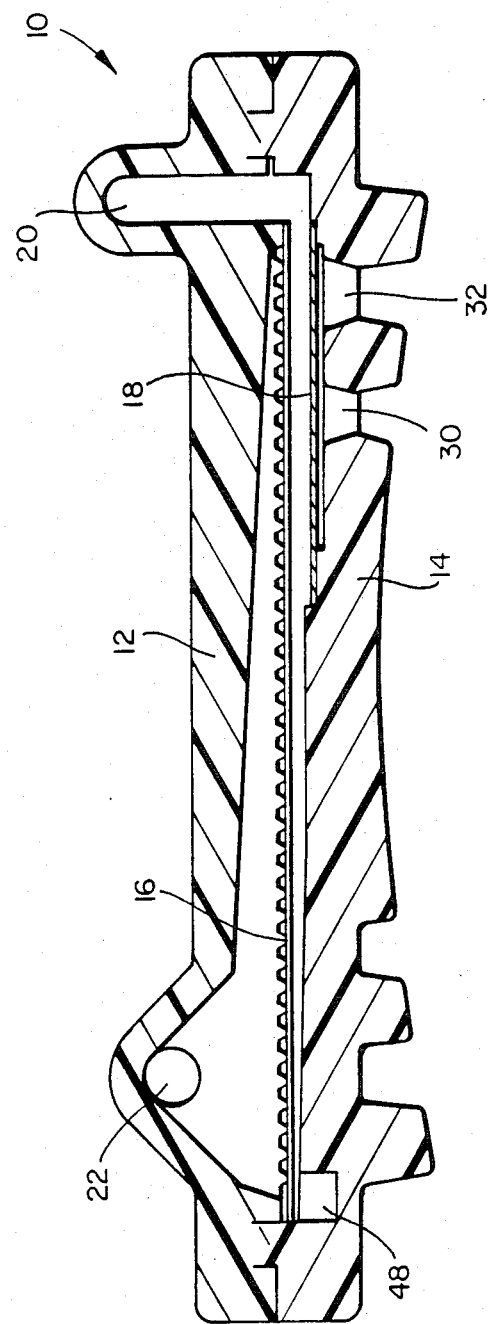

I.V. FILTER APPARATUS

BACKGROUND OF THE INVENTION

This invention relates to a filter holder useful in the filtration of intravenous fluids as they are supplied to patients undergoing intravenous therapy. More particularly, the invention relates to a holder for a microporous membrane filter adapted to separate gases and liquids while performing the filtration function.

Filter holder designs adapted to separate liquids from gases entrained therein while filtering the liquid are known. Specific designs for such filter holders are shown, for example, in U.S. Pat. No. 3,523,408, issued Aug. 11, 1970, to D. Rosenberg, U.S. Pat. No. 3,631,654, issued Jan. 4, 1972 to Riely et al and U.S. Pat. No. 3,854,907 to Rising.

It is necessary to remove air from intravenous fluid before the fluid enters the vein of a patient since bubbles which enter a vein can cause an air embolism with substantial danger of death to the patient. For this reason, filters which perform a liquid-gas separation have found particular application in the in-line filtration of intravenous fluids, i.e., filtration as the fluid is being supplied to the patient. Filtration to remove small particles from intravenous fluids as they are administered also reduces the incidence of phlebitis in patients undergoing intravenous therapy.

In general, in the prior constructions of gas-liquid separating filters, the liquid, containing gases entrained therein, is supplied to a chamber having two outlets, one of which is covered with filtration material which is wetted by the liquid while the other outlet is covered by material which is not wetted by the liquid. The typical small pore size of the wetted filter prevents gas from passing through said filter at the usual operating pressures. However, liquid will not pass through the wetted filter whenever a gas bubble contacts the filter surface. Thus, gas bubbles must be brought into contact with the non-wetted filter. Pressure within the chamber will tend to force gases entrained in the liquid through the non-wetted filter which thus acts as a gas vent.

Filter holders in which the non-wetting filter and the liquid filter oppose each other are shown, for example, in the cited Rosenberg patent. Rosenberg does not provide a means for facilitating the separation of gas and liquid within the filter unit in that there are no means provided for directing gas preferentially toward the hydrophobic filter and for directing the liquid toward the hydrophilic filter. Thus, there exists the possibility of gas accumulating at the hydrophilic filter which can lead to blockage of liquid through the hydrophilic filter. The cited Riely et al patent illustrates filter holder constructions in which the non-wetting and wetting filters are adjacent each other. The prior constructions, such as those illustrated in the foregoing patents, in general, provided a relatively large ratio of non-wetting to wetting filter, the ratio often approaching a value of 1 or even more. They also depend upon the buoyancy of the gas to cause the gas to contact the non-wetting filter. Additionally, the area of the wetted filter was not large in comparison to the filter holder. When, as is usual, microporous filters of the screen type are used in such holders, a relatively large wettable filter area is required to prevent filter clogging when in use. This is particularly true for holders to be used in intravenous therapy, since the available pressure to force liquid through the wetted filter is relatively small, i.e., a pressure corresponding to a liquid head of 3 to 4 feet. Also, filter holders made according to the prior art had relatively large internal volumes to permit entrained gases to move to the surface of the non-wetting filter without blocking the wetting filter, and hence were relatively bulky if they were made large enough to provide the desired wettable filter area; and because of their bulk and their general shape, they were unsuited for general use in intravenous therapy.

The cited Rising patent utilizes a filter holder having a hollow tubular support for the wetted filter. The outlet vent is located at one end of the filter rather than being on one side of the filter to minimize accidental blocking of the vent. The filter holder relies upon the buoyancy of air in liquid to effect air-liquid separation. While the apparatus is easier to manufacture and use as compared to the other available prior art apparatus, separation of air and liquid is dependent upon the position of the apparatus. It also has a relatively large internal volume to allow the gas bubbles to reach the vent filter.

In some forms of intravenous therapy, it is desirable for the liquid administration system to have a low internal volume to reduce the mixing of drugs given consecutively and to reduce the total amount of a drug given to the patient, as when the administration system is filled with heparin to prevent blood from clotting in the catheter between administrations of another drug. Accordingly, it would be desirable to provide a filtration device suitable for use in intravenous liquid administration which has low internal volume and yet prevents gas bubbles from occluding the liquid filter.

SUMMARY OF THE INVENTION

In accordance with this invention, a vented filter holder is provided which is formed by two housing portions, joined at their periphery to form a space between the portions. The space is provided with an inlet and an outlet and a liquid wettable membrane is positioned within the space to seal the inlet from the outlet. A liquid non-wettable membrane which is smaller than the liquid wettable membrane is positioned adjacent the inlet and spaced apart from the liquid wettable membrane. A second space between the liquid wettable membrane and the liquid non-wettable membrane is provided which has a maximum height between about 2 mm and about 0.05 mm adjacent the inlet and a height less than about 0.2 mm furthest from the liquid inlet. At least a portion of the surface opposite the wettable membrane is designed so that it is gradually sloping toward the wettable membrane in a direction away from the liquid inlet. A gas vent is provided adjacent the liquid non-wettable membrane which is adapted to permit passage of gas from the second space to the atmosphere. Because of the tapered surface utilized in this invention, the liquid preferentially travels toward the narrow space due to surface tension, while the gas travels toward the larger portion of the space in the second space, which larger space is positioned adjacent the air vent. A step or rapid reduction in space height adjacent the edge of the air vent impedes the gas from reaching the narrow space initially and facilitates gas-liquid separation.

BRIEF DESCRIPTION OF THE DRAWINGS

FIG. 6 is a cross-sectional view of the filter holder of this invention with the air vent element of FIG. 5.

DESCRIPTION OF SPECIFIC EMBODIMENTS

Figure 1:
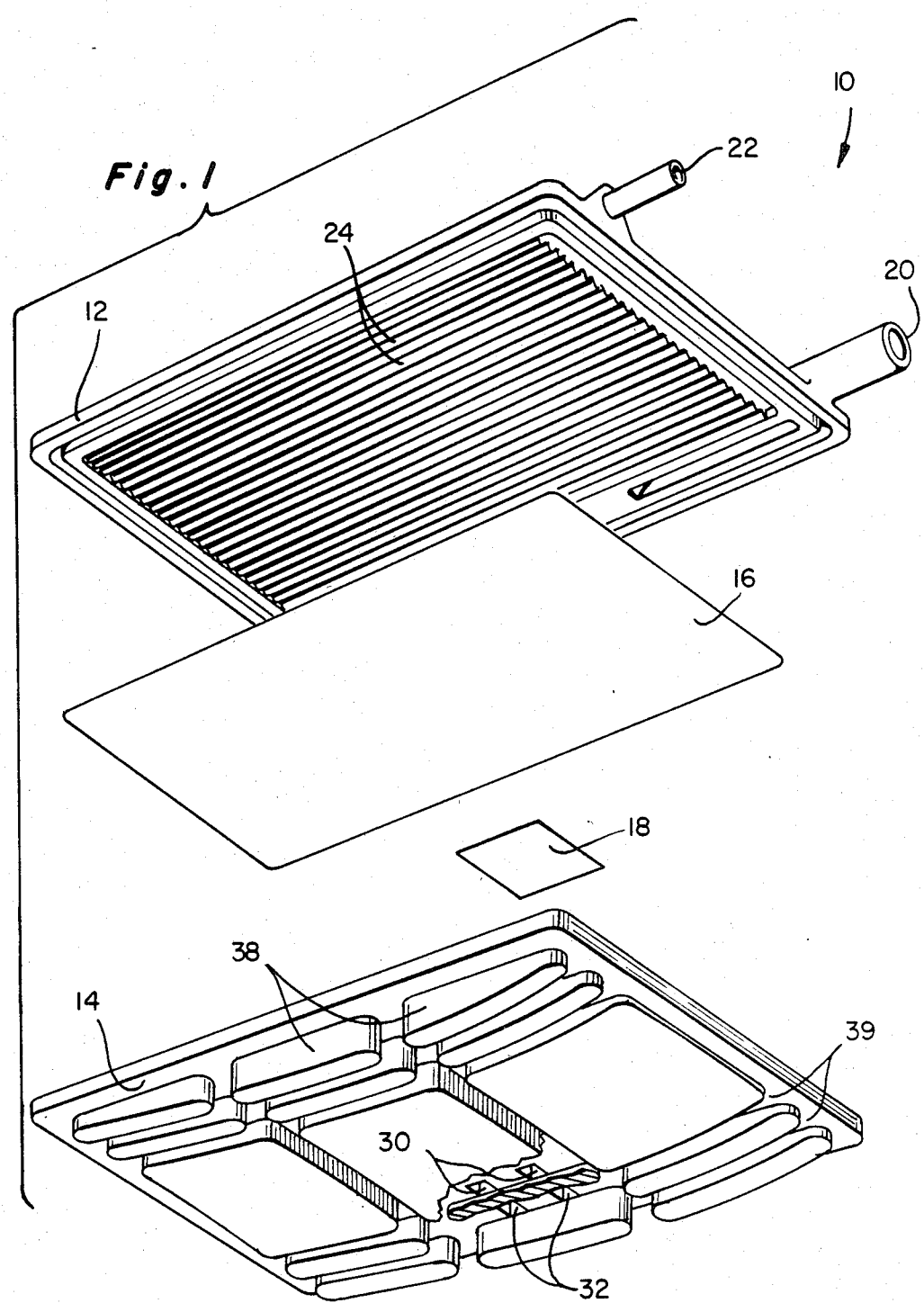
FIG. 1 is an exploded view of the filter holder of this invention.

The filter holder of this invention is based upon the utilization of a space within the filter holder which is in direct communication with the liquid inlet to the filter holder, which space is characterized by a gradually sloping surface to define a smaller cross-section within the space and a larger cross-section within the space. A hydrophobic filter which preferentially permits gas to pass therethrough is provided near the larger portion of the space so that the gas is removed from the filter holder while the remaining liquid within the space is passed through a hydrophilic filter element and thence to an outlet for the filtered liquid. The filtered liquid then is passed intravenously into a patient. The liquid entering the inlet to the filter holder preferentially migrates toward the smaller portion of the space due to surface tension forces, while any gas entrained with the incoming liquid preferentially adheres to the hydrophobic filter or else migrates away from the smaller portion of the space toward the larger portion of the space.

Referring to the Figures, the vented filter holder 10 of this invention includes a first housing portion 12, a second housing portion 14, a hydrophilic membrane 16 and a hydrophobic membrane 18. The first housing portion 12 includes an inlet 20 and a filtrate outlet 22. The first housing portion 12 also includes a ribbed surface 24 which contacts the hydrophilic membrane 16. The ribbed surface 24 promotes passage of filtrate through the membrane 16 and toward the outlet 22 in order to promote filtration. The inlet 20 is in communication with space 26. The inner surface 28 of the second housing portion 14 is preferably hydrophilic in order to promote migration of liquid away from hydrophobic membrane 18. It is preferred to employ a step 29 extending around the perimeter of the hydrophobic membrane 18 to further impede the movement of gas toward the narrow space 27. The portion of space 26 adjacent inlet 20 has a height between the hydrophobic membrane 18 and the hydrophilic membrane 16 of between about 2 mm and about 0.05 mm, preferably between about 1 mm and about 0.2 mm. The inner surface 28 of second housing portion 14 gradually slopes away from the larger space 25 toward the smaller space 27. The smaller space 27 generally has a height less than about 0.3 mm as defined by the distance between the hydrophilic membrane 16 and the inner surface 28 of the second housing portion 14. By controlling the configuration of the space 26 as described, the liquid entering inlet 20 tends to migrate toward space 27 to the exclusion of gas due to surface tension forces while the gas tends to migrate to and be retained within space 25 for passage through hydrophobic membrane 18 out vents 30 and 32. The first housing portion 12 and second housing portion 14 are snap-fit together by tongue and groove fittings 34 and 36 and which can be heat sealed or solvent sealed. It is to be understood that any convenient means for sealing first housing portion 12 and second housing portion 14 can be utilized so long as the liquid entering inlet 20 must pass through membrane 16 before leaving through outlet 22. The second housing portion 14 is provided with a curved surface 38 along the various extensions of the second housing portion so that the vented filter holder of this invention can be conveniently mounted on a patient's arm, leg or the like to conform to the surface of the patient's body. In addition, the channels 39, 30 and 32 effectively permit migration of perspiration and heat as well as vented gases away from the patient during use of the vented filter holder 10 of this invention.

Figure 2:
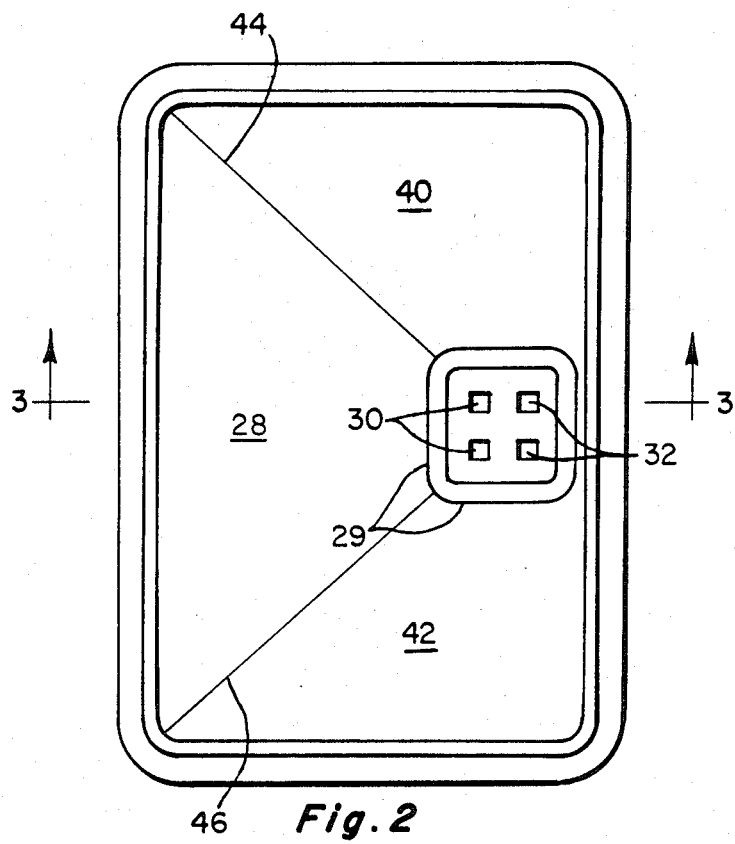
FIG. 2 is a top view of the air vent element of the filter holder of this invention.
Figure 3:
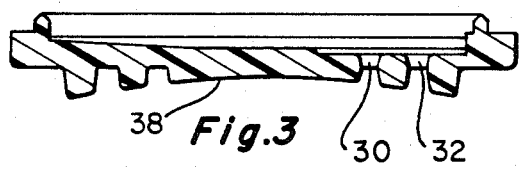
FIG. 3 is a cross-sectional view taken along line 3—3 of FIG. 2.
Figure 4:
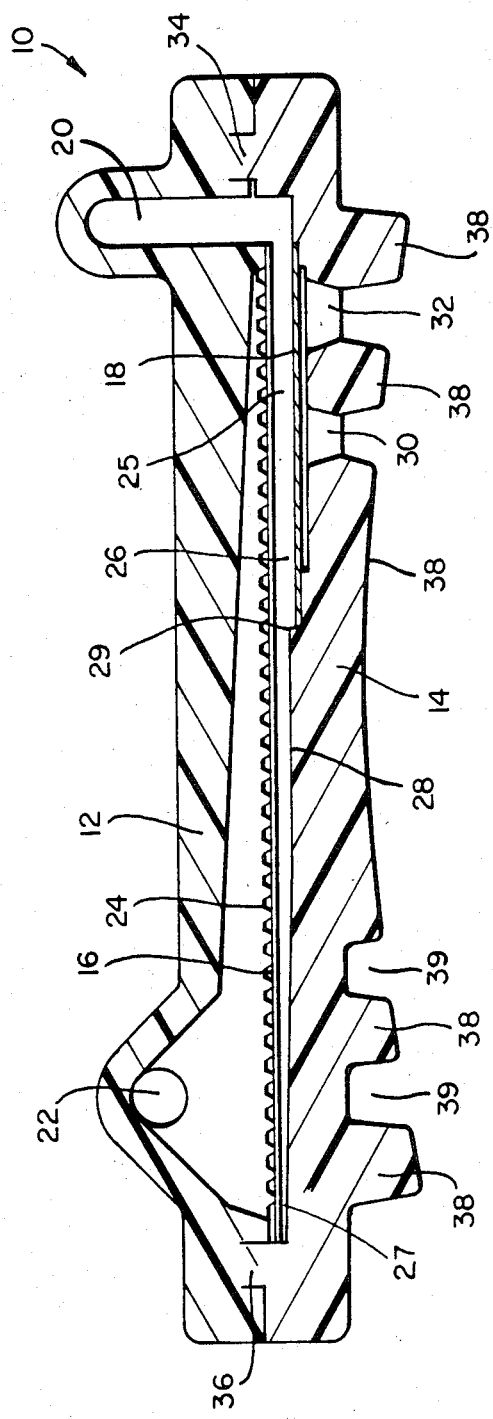
FIG. 4 is a cross-sectional view of the filter holder of this invention.

Referring to FIGS. 2 and 3, the gradually sloping surface 28 can be defined as being sloping including the portions 40 and 42 by means of lines 44 and 46 in order to direct gases in incoming liquid toward vents 30 and 32.

The liquid wettable filter material is preferably a microporous membrane filter made of mixed esters of cellulose. This material is available in a wide range of pore sizes and the particular pore size depends upon the particular use for which the unit is designed. For use in intravenous therapy, it has been found that mean pore sizes in the range 5.0 micrometers to 0.1 micrometers are preferred. Liquid wettable filter material of the foregoing description is available from the Millipore Corporation, Bedford, MA as its type MF filter.

Figure 5:
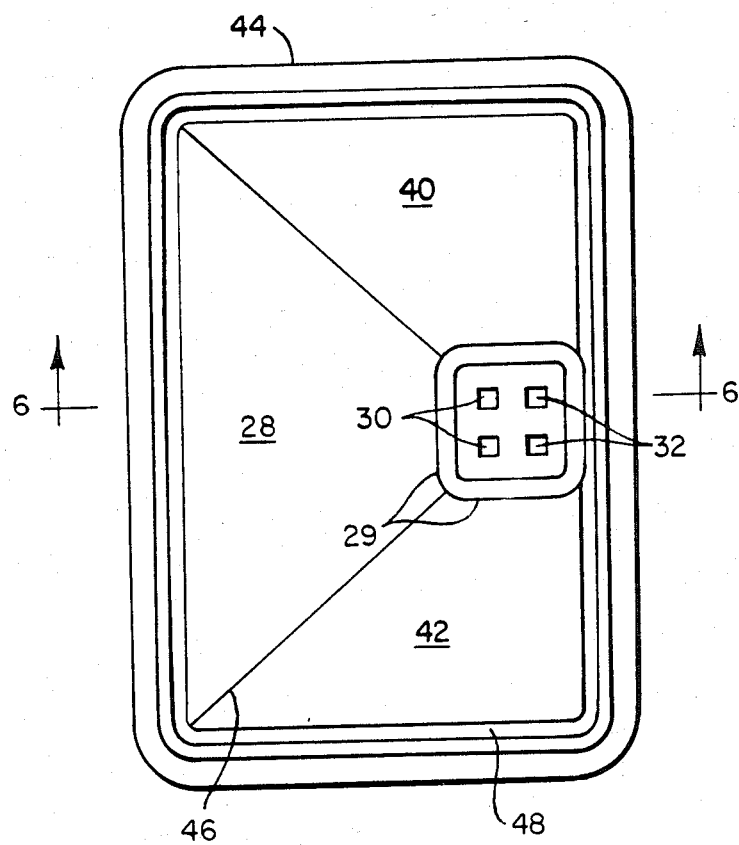
FIG. 5 is a top view of an alternative embodiment of the air vent element.

Referring to FIGS. 5 and 6 wherein like reference numbers correspond to those in FIGS. 1-4, the channel 48 which surrounds the periphery of the hydrophobic membrane 18 facilitates the separation of gas from liquid. The use of the channel 48 is a preferred form of this invention.

The non-wettable filter material may be one of the foregoing materials which has been chemically treated to render it non-wettable. However, it is preferred to use a filter made of polytetrafluoroethylene or polyvinylidene fluoride which is inherently non-wettable. For use in intravenous filter holders made according to this invention, a microporous polytetrafluoroethylene filter having a pore size of 0.2 micrometers has been used. Filters of this material are also available from Millipore Corporation under the trademark Fluoropore as its grade FG.

The filter support member 10 is preferably molded of a polyester resin. This permits both the wettable and non-wettable filters to be heat sealed or solvent sealed directly to the tubular support member in the locations shown. Heat sealing of the filter material might also be accomplished when the support was molded of polyvinylchloride. When the support member is made of a plastic or of metal so that heat sealing is not possible, the filter materials may be bonded to the filter housing portions 12 and 14 with solvents or adhesives as appropriate.

As noted above, the filter holder of this invention is particularly useful in connection with intravenous therapy. In a representative embodiment in which the filter unit member is approximately 1.8 inches in length, 1.3 inches in width and 0.2 inches high, the total active filter area is about 1.5 square inches. In the space 26, the largest height is about 0.3 mm and the smallest height is about 0.01 mm.

In use, the inlet port 20 is connected to a supply of liquid to be filtered, which may be an intravenous fluid. The liquid enters the port 20 and partially fills the space 26 between the second filter housing portion 14 and the filter 16. Any gas bubbles in the system will not readily pass through the wetted membrane 16, but such gas may escape through the non-wetting filter 18 and pass downwardly through the vents 30 and 32. The liquid passes through the filter 16 and into the channels 24. This filtered liquid flows in the grooves to the outlet 22 and then through external tubing (not shown) to the intravenous injection site.

We claim:

1. A vented filter apparatus comprising a first housing portion and second housing portion, said housing portions being joined together about the periphery of said housing portions, thereby to form a space between said portions, an inlet into said space and an outlet from said space, a liquid wettable membrane positioned on a first surface of said first housing portion within said space to seal said inlet from said outlet, said second housing portion having a first surface and a second surface forming a first space section and a second space section, a liquid non-wettable membrane positioned adjacent said inlet on said first surface of said second housing portion within said space and spaced apart from said liquid wettable membrane, said first space section being positioned adjacent said non-wettable membrane and being positioned between said liquid wettable membrane and said second surface, said first space section being positioned adjacent said non-wettable membrane, said second space section being in fluid communication with said first space section and having a maximum height between about 2 mm and about 0.05 mm adjacent said inlet and a height less than about 0.3 mm furthest from said inlet, said second surface within said second space section being hydrophilic and at least a portion of the second surface within said second space section positioned opposite the wettable membrane sloping toward the wettable membrane in a direction away from said inlet such that the height of the second space section adjacent said outlet is always smaller than the height of the first space section adjacent said inlet and a gas vent adjacent said liquid non-wettable membrane adapted to permit passage of gas from said first space section through said non-wettable membrane.

2. The apparatus of claim 1 wherein the first surface opposite the wettable membrane gradually slopes toward the wettable membrane.

3. The apparatus of claim 1 wherein a discrete step is provided about at least a portion of the periphery of said non-wettable membrane.

4. The apparatus of claim 1 wherein the first surface opposite the wettable membrane slopes as discrete steps toward the wettable membrane.

5. The apparatus of any one of claims 1, 2, 3 or 4 wherein said wettable membrane is positioned adjacent a ribbed surface.

6. The apparatus of any one of claims 1, 2, 3 or 4 wherein an outer surface of said apparatus is ribbed and is concave.

7. The apparatus of any one of claims 1, 2, 3 or 4 wherein said wettable membrane is polytetrafluoroethylene.

8. The apparatus of any one of claims 1, 2, 3 or 4 wherein said wettable membrane is a cellulose ester.

9. The apparatus of any one of claims 1, 2, 3 or 4 wherein said non-wettable membrane is polyvinylidene fluoride.

10. The apparatus of claim 1 wherein a channel is provided about at least a portion of the periphery of the wettable membrane.

* * * * *